United States Patent
Brünjes et al.

(10) Patent No.: US 9,790,182 B2
(45) Date of Patent: Oct. 17, 2017

(54) PREPARATION OF PIPERIDINE-4-CARBOTHIOAMIDE

(71) Applicant: Bayer CropScience Aktiengesellschaft, Monheim Am Rhein (DE)

(72) Inventors: Marco Brünjes, Hattersheim Am Markt (DE); Mark James Ford, Wiesbaden-Breckenheim (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/317,923

(22) PCT Filed: Jun. 8, 2015

(86) PCT No.: PCT/EP2015/062650
§ 371 (c)(1),
(2) Date: Dec. 9, 2016

(87) PCT Pub. No.: WO2015/189115
PCT Pub. Date: Dec. 17, 2015

(65) Prior Publication Data
US 2017/0137381 A1    May 18, 2017

(30) Foreign Application Priority Data

Jun. 11, 2014    (EP) ..................... 14172038

(51) Int. Cl.
*C07D 211/60*    (2006.01)
*C07D 211/62*    (2006.01)
*A01N 43/40*    (2006.01)

(52) U.S. Cl.
CPC ............ *C07D 211/62* (2013.01); *A01N 43/40* (2013.01)

(58) Field of Classification Search
CPC .............................. C07D 211/62; A01N 43/40
USPC ........................................................ 546/245
See application file for complete search history.

(56) References Cited

U.S. PATENT DOCUMENTS

2010/0197703 A1    8/2010    Griffioen et al.
2010/0240619 A1    9/2010    Gregory et al.

FOREIGN PATENT DOCUMENTS

| WO | WO-2008/013622 | 1/2008 |
| WO | WO-2009/094407 | 7/2009 |
| WO | WO-2011/072207 | 6/2011 |
| WO | WO-2011/076699 | 6/2011 |
| WO | WO-2011/146182 | 11/2011 |
| WO | WO-2013/127808 | 9/2013 |

OTHER PUBLICATIONS

Gardner et al, Synthesis of Compounds for Chemotherapy of Tuberculosis. VII. Pyridine N-oxides with Sulfur-containing groups, Journal of Organic Chemistry, 1957, vol. 22, p. 984-986.*
Eilhauer H.D. et al. (Aug. 1967). "Zur Trennung von 2- und 3-Äthylisonicotinsäurethioamid," *Archie der Pharmazie* 300(8): 657-659.
Extended European Search Report dated Sep. 1, 2014, for EP Application No. 14172038.3, filed on Feb. 4, 2014, 5 pages.
Gardner et al. (Aug. 1957). "Synthesis of Compounds for Chemotherapy of Tuberculosis. VII. Pyridine N-Oxides with Sulfer-Containing Groups," *Journal of Organic Chemistry* 22:984-986.
International Search Report mailed Jul. 10, 2015, for PCT Application No. PCT/ET2015/062650, filed on Jun. 8, 2015, 9 pages.
Kuroyan R. A. et al. (Jan. 1, 1983). "Synthesis of Thiazoles of the Piperidine Series," *Armîanskiî khimicheskiî zhurnal* 36(9): 610-614. (English translation of abstract is on p. 613).
Eilhauer, H.D. et al. (Aug. 1967). "The Separation of 2- and 3-Ethylisonicotinic Acid Thioamide," *Archiv der Pharmazie* 300(8): 657-659.
Kuroyan R. A. et al. (Jan. 1, 1983). "Synthesis of Thiazoles of the Piperidine Series," *Armîanskiî khimicheskiî zhurnal* 36(9): 610-614.

* cited by examiner

*Primary Examiner* — T. Victor Oh
(74) *Attorney, Agent, or Firm* — Morrison & Foerster LLP

(57) ABSTRACT

The present invention describes a novel process for preparing piperidine-4-carbothioamide.

8 Claims, No Drawings

PREPARATION OF PIPERIDINE-4-CARBOTHIOAMIDE

CROSS REFERENCE TO RELATED APPLICATIONS

This application is the national stage of International Application No. PCT/EP2015/062650, filed internationally on Jun. 8, 2015, which claims the benefit of European Application No. 14172038.3, filed Jun. 11, 2014, the disclosures of which are hereby incorporated by reference in their entireties for all purposes.

The present invention relates to a novel process for preparing piperidine-4-carbothioamide.

Piperidine-4-carbothioamide derivatives are important precursors for active pharmaceutical and agrochemical ingredients (cf. WO 2008/013622, WO 2011/072207 and WO 2011/076699).

The processes referred to in WO 2008/013622 and WO 2011/072207 and, inter alia, also in WO 2011/146182, WO 2009/094407 and US 2010/0240619 for preparing piperidine-4-carbothioamide derivatives all employ N-substituted 4-cyanopiperidine as starting material. However, the disadvantage of these processes is that they require either stoichiometric amounts of a base (e.g. diethanolamine), DMF as solvent, a dry ice condenser or an aqueous work-up (large amounts of waste). It can further be assumed that said processes require a large excess of hydrogen sulphide.

Diethylamine, pyridine and triethylamine are cited as alternative bases in, inter alia, WO 2011/072207 and *Armīānskiĭ khimicheskiĭ zhurnal* 1983, 36, 610-614, likewise the hydrogen sulphide may also be used in the form of one of its salts (sodium sulphide, sodium hydrogen sulphide, etc.). The first-named document refers to a long reaction time (72 hours) in an example reaction described in experimental terms.

A further hydrogen sulphide source that may be employed, as described, for example, in WO 2013/127808 in the synthesis of a substituted piperidine-4-carbothioamide, is ammonium sulphide (stable only as an aqueous solution). This document again describes relatively long reaction times (24 hours) and, furthermore, there is again a need here for aqueous work-up of the DMF reaction solution and also for extraction of the product with subsequent chromatographic purification.

Document US2010/197703 describes a mixture of methanol and tetrahydrofuran instead of the predominantly used dimethylformamide. Aqueous ammonium sulphide is likewise used here. However, the above mentioned disadvantages are encountered here as well, a further problem being the very low yield of only 25%.

The only literature synthesis of piperidine-4-carbothioamide (I), in this regard see *J. Org. Chem.* 1957, 22, 984-986, comprises initially charging a 30% methanolic ammonia solution and the 4-cyanopiperidine and subsequently introducing hydrogen sulphide until complete saturation. However, this process also has disadvantages, for example the additional use of a base (ammonia) and a long reaction time of 48 hours.

The problem addressed by the present invention in view of the prior art described hereinabove is that of providing a process which does not have the aforementioned disadvantages and consequently provides a high yield route to piperidine-4-carbothioamide (I).

It has now been found that the above-described problem is solved by a process for preparing piperidine-4-carbothioamide of formula (I),

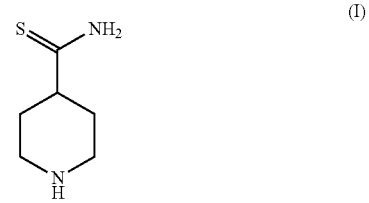

characterized in that 4-cyanopiperidine of formula (II),

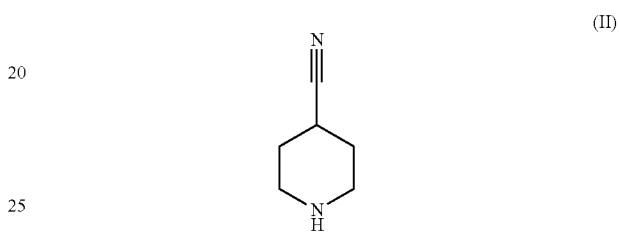

is reacted with hydrogen sulphide (III) in the presence of a solvent to afford the compound of formula (I).

Surprisingly, the piperidine-4-carbothioamide of formula (I) is obtained in good yields and high purity in various solvents without addition of a further base, the process according to the invention thus overcoming the abovementioned disadvantages of the prior art methods of preparation. This reaction is preferably carried out in a sealed reaction vessel.

PROCESS DESCRIPTION

Scheme 1:

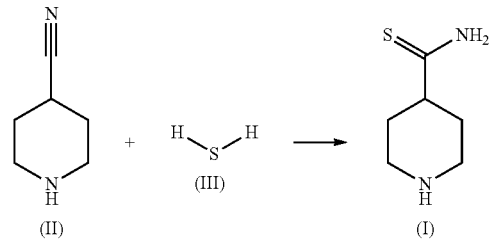

Piperidine-4-carbothioamide (I) is prepared by reacting 4-cyanopiperidine (II) with hydrogen sulphide (III) in a suitable solvent at a temperature of $\geq 0°$ C. in a sealed reaction vessel.

Suitable solvents are solvents selected from the group consisting of ethers (e.g. tetrahydrofuran, diethyl ether, methyl tert-butyl ether), aliphatics and aromatics (e.g. heptane, cyclohexane, benzene, toluene or xylene), alcohols (e.g. methanol, ethanol, isopropanol, n-butanol, i-butanol, tert-butanol, cyclopentanol, cyclohexanol), amides (e.g. dimethylformamide, dimethylacetamide), water and also mixtures thereof. Among these, preference is given to alcohols, both primary and secondary but also tertiary alcohols. Particular preference is given to alcohols comprising from 1 to 10 carbon atoms. Very particular preference is given to methanol, ethanol, isopropanol, n-butanol, i-butanol, cyclohexanol, cyclopentanol. n-Butanol is specifically preferable. Methanol is further specifically preferable. Ethanol is further specifically preferable. Isopropanol is further specifically preferable. i-Butanol is further specifically preferable. Cyclohexanol is further specifically preferable. Cyclopentanol is further specifically preferable.

Hydrogen sulphide (III) is introduced into the reaction vessel in gaseous form and the reaction vessel internal pressure is monitored and adjusted to a pressure in a range between 0 and 10 bar (relative pressure). Typically, depending on its solubility in the particular solvent employed, hydrogen sulphide (III) needs to be employed in at least an equimolar amount or in excess (1.00 to 10 equivalents, preferably 1.1 to 5 equivalents, more preferably 1.5 to 3 equivalents) based on the compound of formula (II).

The process according to the invention is typically carried out at between 0° C. and 200° C., preferably in the range between 20° C. and 100° C., more preferably between 40° C. and 80° C.

The reaction time is typically between 30 minutes and 24 hours, preferably between 2 and 12 hours.

Work-up and isolation of the compound of formula (I) typically comprises cooling down the reaction mixture to a temperature range between −20° C. and 25° C. to bring down the compound of formula (I) as precipitate. Any remaining overpressure is released and the precipitate is filtered off, washed with the particular solvent employed and dried.

Subjecting the compound of formula (I) thus obtained to treatment with acids affords the corresponding salts.

Example Preparation of Piperidine-4-Carbothioamide

In a 250 ml pressure reactor, 100 ml of n-butanol and 25 g of cyanopiperidine (220 mmol) are heated to 60° C. and hydrogen sulphide is then introduced into the reactor to maintain a constant overpressure of 4 bar (a total of 17.5 g (513 mmol) of hydrogen sulphide is introduced into the reactor during the reaction time). After 6 hours no more hydrogen sulphide is introduced, and the reaction mixture is stirred at 60° C. for a further 6 hours and then cooled down to 10° C. over 2 hours. Excess hydrogen sulphide is released via a chlorine bleach scrubber, the gas space of the reactor is then purged with nitrogen for 15 minutes and the solid brought down is then filtered off with suction via a glass suction filter. The solid obtained is washed once with n-butanol and dried with suction before being fully dried under vacuum at 40° C.

This affords 29.9 g (207 mmol, 90% of theory) of the desired product, piperidine-4-carbothioamide (I), in 97% purity ($^1$H NMR).

$^1$H NMR (DMSO-$d_6$, 600 MHz) δ=9.31 (1H, bs), 9.04 (1H, bs), 2.94 (2H, m), 2.50 (1H, m), 2.43 (m, 2H), 2.30 (bs, 1H), 1.58 ppm (m, 4H);

$^{13}$C NMR (DMSO-$d_6$, 125 MHz) δ=212.1, 50.2, 45.5, 32.2 ppm.

The same reaction carried out with alternative solvents gives the yields and purities reported hereinbelow:

| Solvent | Temp./overpressure/eq. $H_2S$ | Yield | Purity ($^1$H NMR) |
| --- | --- | --- | --- |
| methanol | 60° C./4 bar/3.2 | 85% | 98% |
| ethanol | 60° C./4 bar/2.0 | 94% | 96% |
| 2-propanol | 60° C./4 bar/2.0 | 87% | 98% |
| n-butanol | 60° C./4 bar/2.3 | 90% | 97% |
| 2-butanol | 60° C./4 bar/1.9 | 85% | 98% |
| 1-pentanol | 60° C./4 bar/2.0 | 80% | 96% |
| cyclopentanol | 60° C./4 bar/2.3 | 94% | 97% |

The invention claimed is:

1. A process for preparing a compound of formula (I)

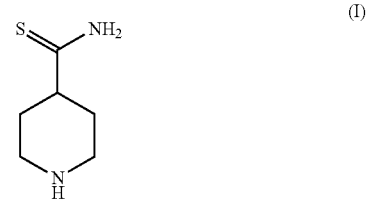

comprising reacting a compound of formula (II)

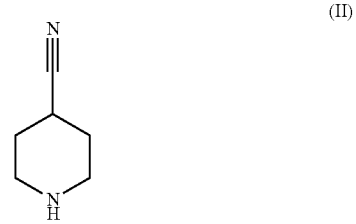

with hydrogen sulfide (III) in the presence of a solvent and without addition of a further base to give the compound of formula (I).

2. The process according to claim 1, wherein the reaction is carried out in a sealed reaction vessel.

3. The process according to claim 1, wherein the reaction is carried out at a reaction temperature of ≥0° C.

4. The process according to claim 1, wherein the solvent comprises a primary alcohol, a secondary alcohol, a tertiary alcohol, or a mixture thereof.

5. The process according to claim 1, wherein the solvent is an alcohol having from 1 to 10 carbon atoms.

6. The process according to claim 1, wherein the solvent is methanol, ethanol, isopropanol, tert-butanol, i-butanol, n-butanol, cyclopentanol, or cyclohexanol.

7. The process according to claim 1, wherein the reaction is carried out at a reaction temperature from 20° C. to 100° C.

8. The process according to claim 1, wherein the reaction is carried out at a reaction temperature from 40° C. to 80° C.

* * * * *